(12) United States Patent
Jesser

(10) Patent No.: US 7,075,435 B2
(45) Date of Patent: Jul. 11, 2006

(54) RFID TAG ASSEMBLY AND SYSTEM

(75) Inventor: Edward A. Jesser, Los Gatos, CA (US)

(73) Assignee: Escort Memory Systems, Scotts Valley, CA (US)

(*) Notice: Subject to any disclaimer, the term of this patent is extended or adjusted under 35 U.S.C. 154(b) by 693 days.

(21) Appl. No.: 09/925,228

(22) Filed: Aug. 8, 2001
(Under 37 CFR 1.47)

(65) Prior Publication Data

US 2004/0046663 A1 Mar. 11, 2004

Related U.S. Application Data

(60) Provisional application No. 60/224,932, filed on Aug. 11, 2000.

(51) Int. Cl.
*G08B 13/14* (2006.01)

(52) U.S. Cl. ............................... 340/572.1; 340/572.7; 340/572.8

(58) Field of Classification Search ............. 340/572.1, 340/572.4, 572.5, 572.7, 572.8, 5.92, 10.1, 340/10.51, 572.6
See application file for complete search history.

(56) References Cited

U.S. PATENT DOCUMENTS

| 5,572,226 | A | | 11/1996 | Tuttle |
| 6,100,804 | A | * | 8/2000 | Brady et al. ............. 340/572.7 |
| 6,140,146 | A | | 10/2000 | Brady et al. |
| 6,687,131 | B1 | * | 2/2004 | Miehling .................... 361/760 |
| 6,717,248 | B1 | * | 4/2004 | Shin et al. ................... 257/678 |
| 6,731,010 | B1 | * | 5/2004 | Horiuchi et al. ............ 257/777 |
| 6,816,380 | B1 | * | 11/2004 | Credelle et al. ............ 361/736 |

* cited by examiner

*Primary Examiner*—Toan N. Pham
(74) *Attorney, Agent, or Firm*—Francis Law Group

(57) ABSTRACT

An RFID tag assembly and system including a first substrate, at least one passive loop disposed on the substrate, the passive loop being adapted to receive and transmit at least one RFID signal, and at least one RFID tag member, the tag member including a second substrate having first and second surfaces and at least one RFID tag disposed on the second substrate first surface, the second substrate second surface being removably secured to one of the first substrate surfaces proximate the passive loop, the RFID tag being coupled to the passive loop.

9 Claims, 4 Drawing Sheets

RFID TAG ASSEMBLY AND SYSTEM

CROSS REFERENCE TO RELATED APPLICATIONS

This application claims the benefit of U.S. Provisional Application No. 60/224,932, filed Aug. 11, 2000.

FIELD OF THE INVENTION

The present invention relates in general to radio frequency identification (RFID) devices, and more particularly to a multi-functional RFID tag assembly and system.

BACKGROUND OF THE INVENTION

RFID systems are well known in the art. Such systems include relatively large packages containing battery powered transmission/receiving circuitry, such as the identification system disclosed in U.S. Pat. No. 4,274,083, to passive systems in which the transceiver receives its power from the base station or interrogator, such as the identification system disclosed in U.S. Pat. No. 4,654,658.

A typical RFID system is made up of reusable tags fixed to or embedded in product carriers, antennas that interrogate the tags via a RF link and a controller. The host (or computer) system interfaces with the controller and directs the interrogation of the tags.

RFID tags provide effective means of identifying, monitoring and controlling materials in a closed loop process. In the factory, tags are employed as the transport mechanism between "islands of automation," providing a record of each process which can be acted upon immediately or downloaded later for analysis.

The tags can be powered by an internal battery (i.e., an "active" tag) or by inductive coupling (i.e., a "passive" tag). Passive tags have zero maintenance and virtually unlimited life. The life span of an active tag is, however, limited by the lifetime of the battery, although some tags offer replaceable batteries.

RFID tags are packaged in a variety of forms and are fastened by a multitude of means. The tags are typically encapsulated for durability against shock, fluids, dust or dirt.

There are, however, several drawbacks associated with conventional RFID tags. First, the tags have limited applicability due to range limitations. Second, as indicated above, the tags are typically permanently fixed to or embedded in the product carriers (e.g., shipping containers). Thus, any data acquired during packaging and/or shipping does not accompany the product upon removal from the shipping container.

It is therefore an object of the present invention to provide a RFID tag assembly and system that provides means for tracking a product or other article after removal from a transport medium.

It is another object of the invention to provide a RFID tag assembly and system that extends the operating range of a conventional RFID tag.

It is yet another object of the invention to provide a RFID tag assembly and system that reduces orientation sensitivity of a conventional RFID tag.

SUMMARY OF THE INVENTION

In accordance with the above objects and those that will be mentioned and will become apparent below, the RFID tag assembly and system in accordance with this invention comprises a first substrate having first and second surfaces, at least one passive loop disposed on at least one of the substrate surfaces, the passive loop being adapted to receive and transmit at least one RFID signal, and at least one RFID tag member, the tag member including a second substrate having first and second surfaces and at least one RFID tag disposed on the second substrate first surface, the second substrate second surface being removably secured to one of the first substrate surfaces proximate the passive loop, the RFID tag being magnetically coupled to the passive loop and having a first operating frequency.

In an additional embodiment of the invention, the second substrate second surface includes adhesive means for re-attaching the RFID tag member to an article or other item.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAIL DESCRIPTION OF THE INVENTION

The RFID tag assembly and system of the present invention substantially reduces or eliminates the disadvantages and shortcomings associated with prior art RFID tags. According to the invention, a conventional RFID tag is disposed proximate and in communication with a larger passive loop (i.e., antenna means) that significantly extends the operating range and reduces orientation sensitivity of the tag. In additional embodiments of the invention, the tag is adapted to be removed and secured to an article (e.g., product container, product, etc.) for tracking purposes.

Figure 1:
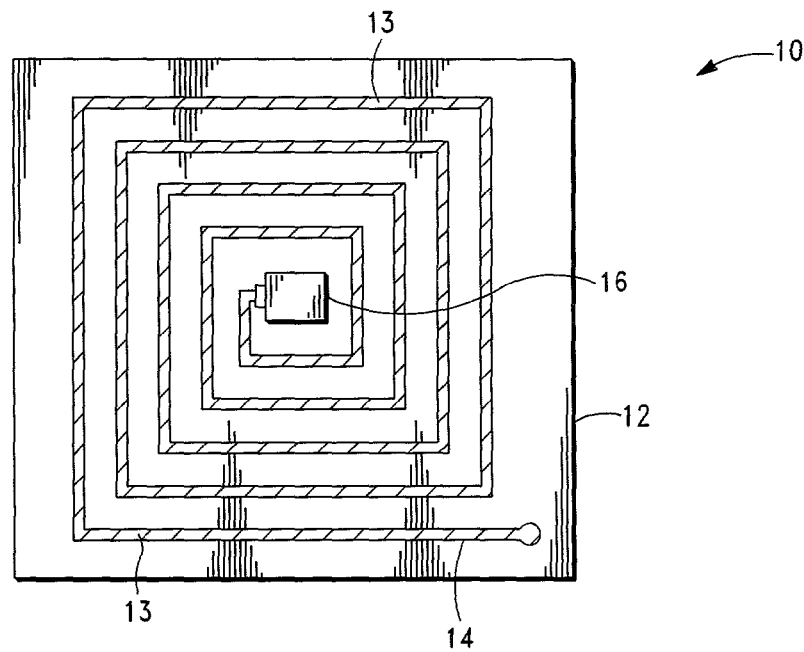
FIGS. 1–3 are plan views of prior art RFID tags.

Referring now to FIG. 1, there is shown a prior art RFID tag 10. By the term "RFID tag" it is meant to mean and include radio frequency identification tags, smart labels and inlets.

As illustrated in FIG. 1, the RFID tag 10 includes a substrate 12 having one or more conductors or circuits 13 and capacitors (referred to herein generally as a conductor system 14) thereon and a RFID chip (or die) 16. The substrate 12 typically comprises a rigid or flexible PC board with the RFID chip 16 affixed thereto.

Figure 2:
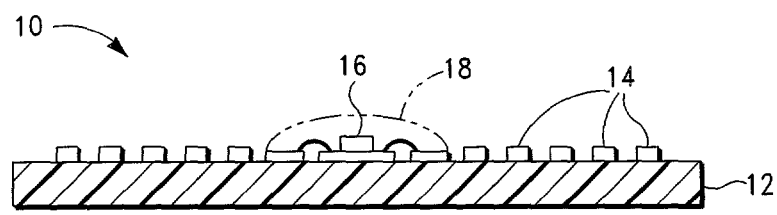

Referring to FIG. 2, the chip 16 is in communication (i.e., electrically coupled) with the conductor system 14 (e.g., die-bonded) and is typically covered with a protective coating. The tag 10, in some instances, is further covered (partially or fully) with an anti-static coating or encapsulated in a protective package.

Figure 3:
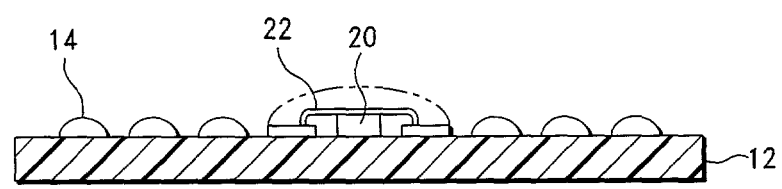

As illustrated in FIG. 2, the chip 16 is generally hard wired to the conductor system 14. However, as illustrated in FIG. 3, the chip may comprise a bumped chip 20 on a carrier 22 that is in direct communication with the conductor system 14.

Various conductor system circuit materials and configurations are typically employed. For example, the circuit 13 can be created in a copper layer on the surface of the substrate 12, created in a stamped or edged metal layer that is laminated onto the substrate 12, created in a layer of conductive paint that is applied (i.e., screened) on the surface of the substrate 12, and/or created in a path of wire placed in a specific pattern and attached to the surface of the substrate 12.

Figure 4:
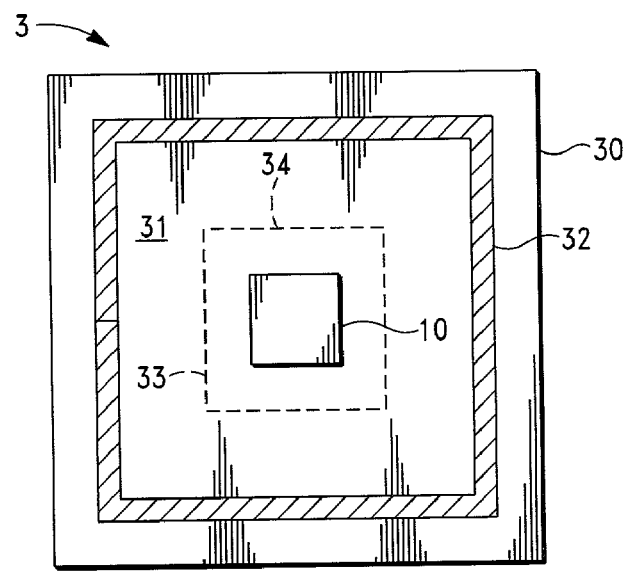
FIG. 4 is a plan view of one embodiment of the RFID tag assembly according to the invention.

Referring now to FIG. 4, there is shown a first embodiment of the RFID tag assembly 3 according to the invention. As illustrated in FIG. 4, the tag assembly 3 includes a substrate 30, a conventional RFID tag 10 and at least one conductive member (i.e., antenna means), such as a passive loop or dipole 32, adapted to transmit and receive RFID signals. As discussed in detail below, the tag 10 and passive loop 32 are preferably disposed on at least one surface or portion of the substrate 30.

According to the invention, the substrate 30 preferably comprises a non-conductive material, such as paper, synthetic paper, polyamide, polyester, Teflon™, ABS™, and like materials. In a preferred embodiment of the invention, the substrate 30 comprises paper.

Figure 5:
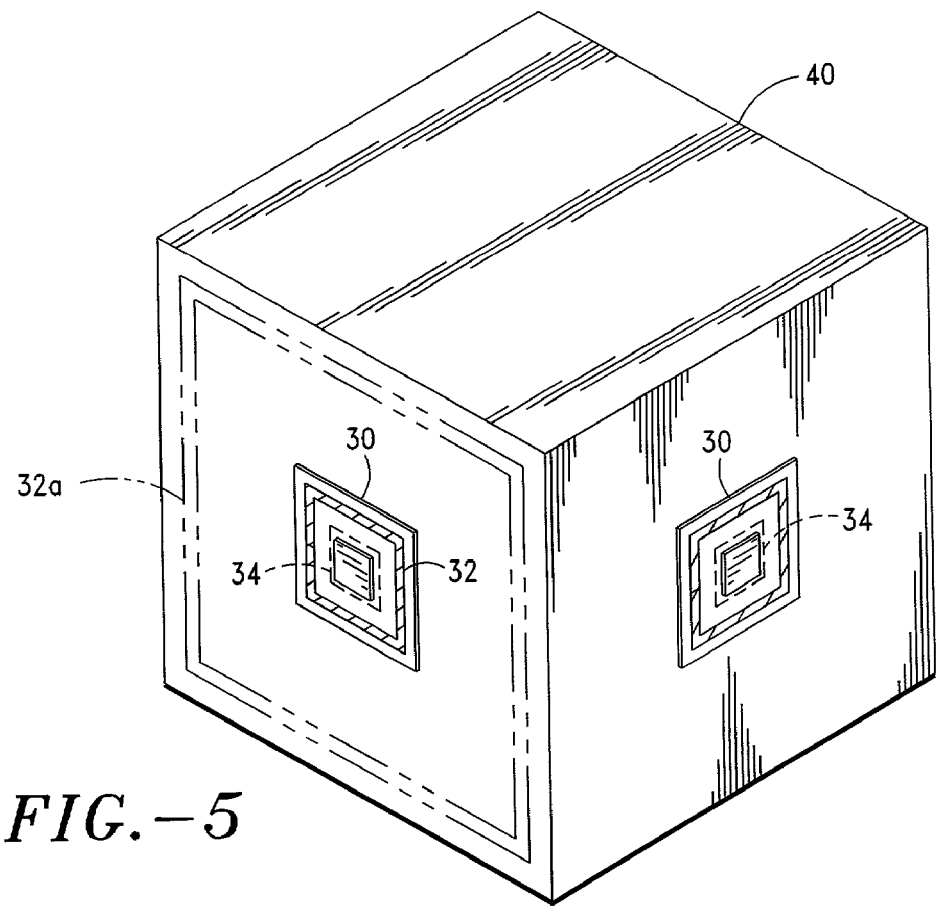
FIG. 5 is a perspective view of one embodiment of the RFID tag system according to the invention.

To facilitate attachment of the substrate 30 to a shipping container 40, such as illustrated in FIG. 5, or other article the substrate 30 preferably includes conventional adhesive means (e.g., two sided tape) disposed on at least one surface or portion of the substrate 30, more preferably, on a surface opposite of the tag 10 and passive loop 32. According to the invention, the substrate 30 can also be secured or directly bonded to a container or other article via conventional adhesives (e.g.,epixy) or conventional mechanical means.

According to the invention, the passive loop 32 is in communication with (i.e., coupled to) the tag 10. As will be appreciated by one having ordinary skill in the art, the loop 32 can be coupled to the tag 10 by various conventional means. In a preferred embodiment of the invention, the loop 32 is magnetically coupled to the tag 10.

The passive loop 32 can comprise various sizes and configurations, such as the substantially square shaped loop shown in FIG. 4. The loop 32 can also be substantially larger than the tag 10 and, hence, is merely limited by the size of the substrate 30.

The passive loop 32 can also be constructed from various conductive materials that can be applied to or embedded in the substrate 30 by conventional means. For example, the passive loop 32 can comprise a carbon/graphite bearing conductive ink that is printed or silk-screened on the substrate 30, comprise a metalized paint directly applied to the substrate 30, a substantially metalized or metallic foil (or wire) bonded to the substrate 30 or a foil or wire embedded in the substrate 30. In a preferred embodiment of the invention, the passive loop 32 comprises a copper foil that is bonded to the substrate 30 by conventional means.

In additional envisioned embodiments of the invention, a separate or additional passive loop 32a can be disposed directly on or embodied in a least one surface of a shipping container 40 (shown in phantom in FIG. 5) or other product containment means.

Referring back to FIG. 4, according to the invention, the RFID tag 10 is preferably disposed proximate the passive loop 32 to facilitate communication to and from the tag 10 and loop 32. In a preferred embodiment of the invention, the tag 10 is disposed in the interior region 31 defined by the loop 32 (hereinafter referred to as the "loop region").

As will be appreciated by one having ordinary skill in the art, virtually all conventional RFID tags (e.g., 2.45 GHz, 125 KHz, 13.5 MHz, 900 MHz) can be employed within the scope of the present invention. Such tags are described in numerous prior art references, including U.S. Pat. Nos. 6,121,878; 6,118,379; and 6,100,804, which are incorporated by reference herein.

According to the invention, the passive loop 32 has an inductance and a capacitance that is tuned to or close to the operating frequency of the respective tag 10. In additional envisioned embodiments of the invention, the passive loop 32 has a distributed capacitance, or a combination of fixed and distributed capacitance that is tuned to or close to the operating frequency of the tag 10.

A key feature of the present invention is the ability of the tag 10 to be removed from the substrate 30 and secured to an article, such as a product or product container. Thus, information and data acquired during packaging, inventory or transport remains with the article through subsequence processes or use. As will be appreciated by one having ordinary skill in the art, the article can be a product or item contained in a larger shipping container, a product container transported in a larger container (e.g., shipping container), or a product container transported on a pallet.

Referring now to FIG. 4, the substrate 30 thus preferably includes means for detaching the tag 10 from the substrate 30. As will be appreciated by one having ordinary skill in the art, various means may be employed to facilitate the detachment of the tag 10 from the substrate 30. In one embodiment of the invention, the substrate 30 includes a substantially continuous line of perforations 33 disposed proximate the tag 10 that define a separable section 34.

According the invention, the separable substrate section or tag assembly 34 preferably includes conventional adhesive means on the rear portion thereof for subsequent attachment of the tag 10 to a product, container or other desired article (discussed in detailed below). However, as will be appreciated by one having ordinary skill in the art, the tag assembly 34 can also be attached to a product or other article by mechanical means.

Figure 6:
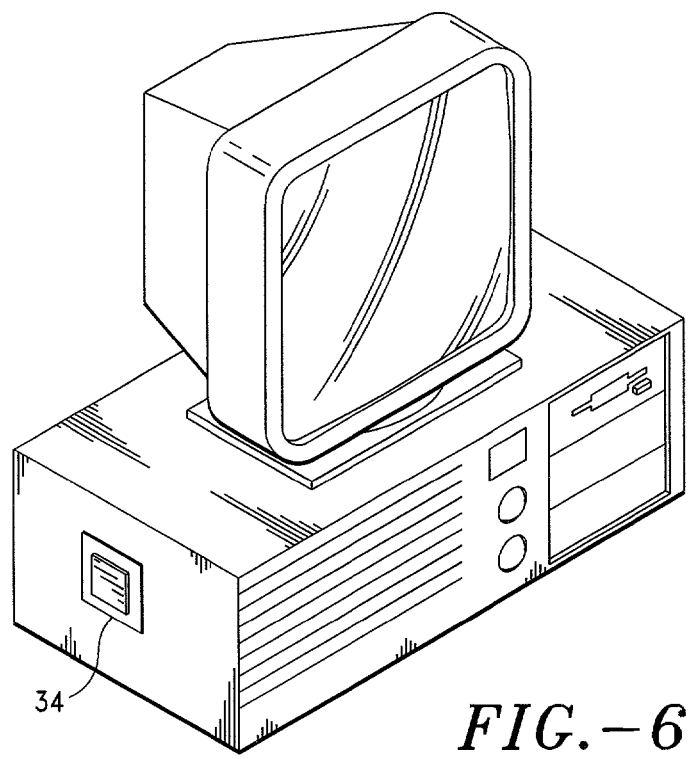
FIG. 6 is a perspective view of an article having a removable RFID tag thereon according to the invention.

Referring now to FIGS. 5 and 6, there is shown one embodiment of the RFID tag system according to the invention. In the noted embodiment one or more of the tag assemblies 34 are initially attached to the shipping container 40. When the product, such as the computer 50 illustrated in FIG. 6, is removed from the shipping container 40, the tag assembly 34 is removed from the substrate 30 and placed on the product 50. Thus, any data or information acquired while the product 50 is in the shipping container 40 remains with the product 50 throughout its lifetime.

Figure 7:
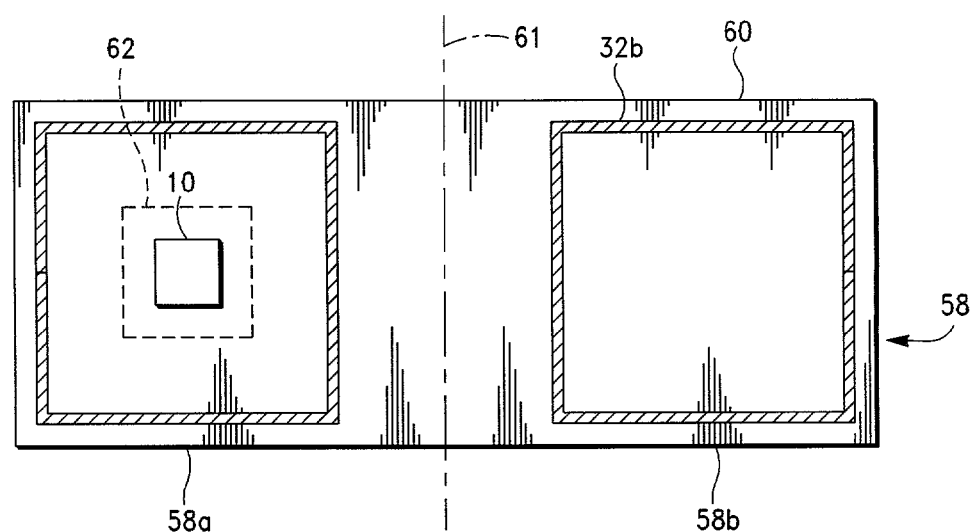
FIGS. 7 and 8 are plan views of further embodiments of the invention.
Figure 8:
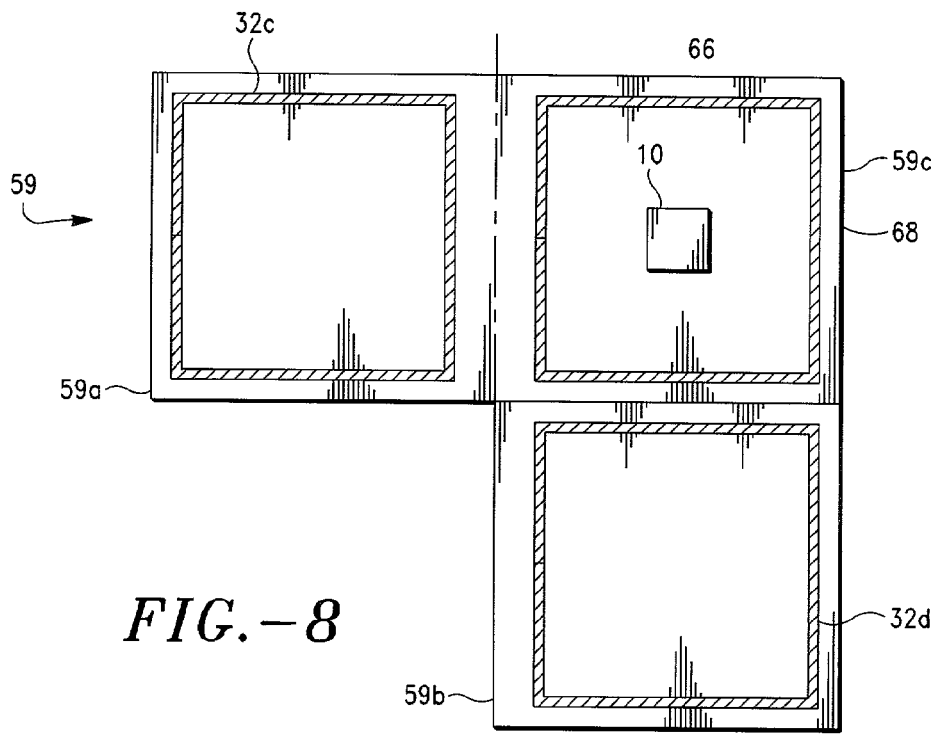

Referring now to FIGS. 7 and 8, there are shown further embodiments of RFID tag systems according to the invention. In addition to increasing the operating range of the tags 10 associated therewith, the noted embodiments substantially reduce the orientation sensitivity that is commonly associated with the tags 10.

Referring now to FIG. 7, there is shown an embodiment of a substrate/tag assembly 58 comprising a substantially linear substrate 60 having at least one tag assembly 62 and at least a second passive loop 32b disposed thereon. As illustrated in FIG. 7, the tag assembly 62 and second passive loop 32b are preferably disposed on opposing ends (i.e., substrate panels 58a, 58b) of the substrate 60 and are preferably in communication with each other.

Figure 9:
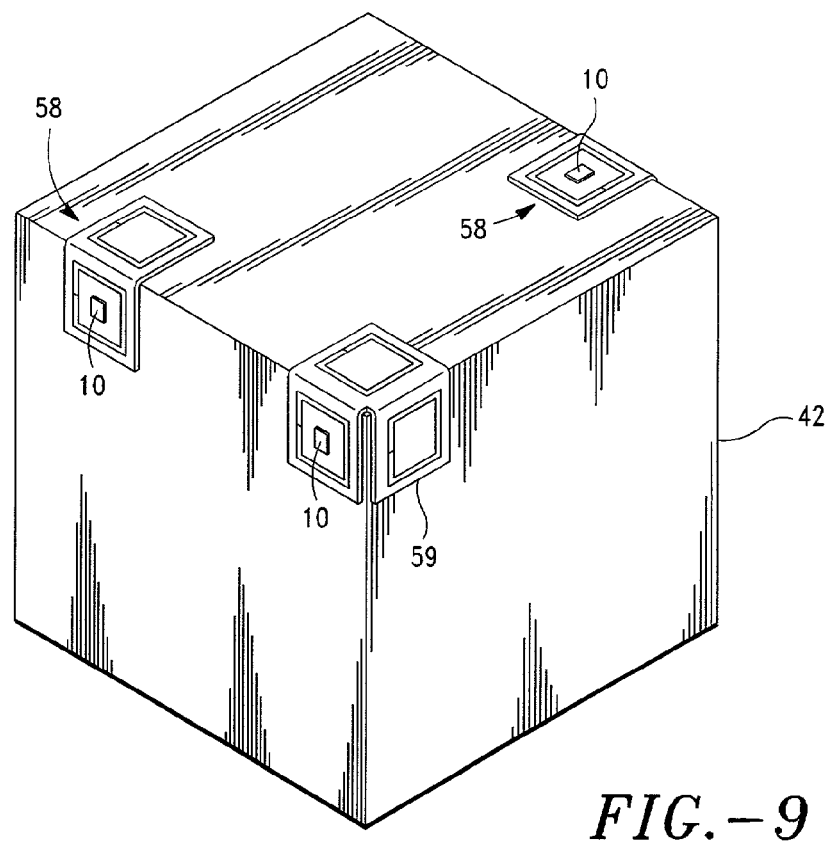
FIG. 9 is a perspective view of a further embodiment of the RFID tag assembly according to the invention.

As further illustrated in FIG. 7, the substrate 60 preferably includes a fold line 61 that facilitates folding of the substrate 60 in a substantially "L" shaped configuration. Referring now to FIG. 9, after the substrate 60 is folded, the substrate/tag assembly 58 can be disposed on one edge of a shipping container 42 to facilitate optimal transmission and receipt of RF signals in at least two planes.

As illustrated in FIG. 9, two or more substrate/tag assemblies 58 can also be employed within the scope of the invention (i.e., disposed on different edges of the container 42) to further reduce the orientation sensitivity of the tags 10 and, hence, RFID system.

Referring now to FIG. 8, there is shown a 3-D substrate/tag assembly 59 having at least one tag assembly 66 and two additional passive loops 32c, 32d disposed on a "multi-panel" substrate 68. The noted tag assembly 66 and loops 32c, 32d are preferably disposed on the substrate legs or panels 59a, 59b, 59c and are similarly in communication with each other.

As illustrated in FIG. 9, the "multi-panel" substrate 68 is flexible enough to be bent proximate each panel 59a, 59b, 59c upon application to the shipping container 42. Thus, for a packaged product, the substrate/tag assembly 59 can be embedded as flexible tag capable of being applied proximate a corner of a product, inner packaging, or outer shipping container 42 to facilitate optimal transmission and receipt of RF signals in at least three planes.

The implementation of the noted substrate/tag assemblies may be one large loop (with suitable resonating capacitance) attached directly to the RFID chip 16, or as two or three resonant loops coupled magnetically to another loop in order to collect the energy from two or more resonant loops and convey it back to the RFID chip 16. As discussed above, the coupling mechanism for this collection loop into the RFID chip 16 may be by direct connection, or through magnetic coupling into another resonant loop directly attached to RFID chip.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A RFID tag assembly, comprising;
a first substrate having first and second surfaces;
at least one passive loop disposed on at least one of said first substrate surfaces, said passive loop being adapted to receive and transmit at least one RFID signal; and
at least one RFID tag member, said tag member including a second substrate having first and second surfaces and at least one RFID tag disposed on said second substrate first surface, said second substrate second surface being removably secured to one of said first substrate surfaces proximate said passive loop, said RFID tag having a first operating frequency, said RFID tag being magnetically coupled to said passive loop.

2. The RFID tag assembly of claim 1, wherein said passive loop is embedded in said first substrate.

3. The RFID tag assembly of claim 1, wherein said second substrate second surface includes first adhesive means for attaching said tag member to an article.

4. The RFID tag assembly of claim 1, wherein said passive loop has an inductance and a fixed capacitance that is substantially equal to said first operating frequency.

5. The RFID tag assembly of claim 1, wherein at least one of said first substrate surfaces includes second adhesive means for attaching said first substrate to an article.

6. A RFID tag assembly for a shipping container having a plurality of surfaces and at least one passive loop disposed on at least one of the container surfaces, said passive loop being adapted to receive and transmit at least one RFID signal, comprising;
a first substrate having first and second surfaces; and
at least one RFID tag member, said tag member including a second substrate having first and second surfaces and at least one RFID tag disposed on said second substrate first surface, said second substrate second surface being removably secured to one of said first substrate surfaces, said RFID tag having a first operating frequency, said first substrate and said RFID tag member being disposed on at least one of said container surfaces proximate said passive loop, said RFID tag being magnetically coupled to said passive loop.

7. The RFID tag assembly of claim 6, wherein said second substrate second surface includes adhesive means for attaching said tag member to an article.

8. A RFID tag assembly for a shipping container having a plurality of surfaces and at least one RFID tag disposed on or embedded in one the container surfaces, comprising;
a first substrate having first and second surfaces; and
at least a first passive loop disposed on at least one of said substrate surfaces, said passive loop being adapted to receive and transmit at least one RFID signal,
said substrate and said passive loop being disposed on at least one of said container surfaces proximate said RFID tag, said passive loop being magnetically coupled to said RFID tag.

9. The RFID tag assembly of claim 8, wherein said tag assembly includes at least a second passive loop disposed on at least one of said container surfaces, said second passive loop being in communication with said first passive loop.

* * * * *